US00PP28634P2

(12) United States Plant Patent
Sakuramoto

(10) Patent No.: US PP28,634 P2
(45) Date of Patent: Nov. 14, 2017

(54) CARNATION PLANT NAMED 'HILBEAOLWILD'

(50) Latin Name: ***Dianthus* L.**
Varietal Denomination: Hilbeaolwild

(71) Applicant: Masahiko Sakuramoto, Minami-Alps (JP)

(72) Inventor: Masahiko Sakuramoto, Minami-Alps (JP)

( * ) Notice: Subject to any disclaimer, the term of this patent is extended or adjusted under 35 U.S.C. 154(b) by 0 days.

(21) Appl. No.: 15/330,014

(22) Filed: Jul. 25, 2016

(51) Int. Cl.
*A01H 5/02* (2006.01)

(52) U.S. Cl.
USPC ..... Plt./273

(58) Field of Classification Search
USPC ..... Plt./273
See application file for complete search history.

*Primary Examiner* — Annette Para
(74) *Attorney, Agent, or Firm* — C. A. Whealy

(57) ABSTRACT

A new and distinct cultivar of Carnation plant named 'Hilbeaolwild', characterized by its compact, uniformly mounding and upright to broadly spreading plant habit; relatively small leaves; freely flowering habit; bright pink-colored single flowers with light pink-colored margins; and good container and garden performance.

1 Drawing Sheet

Botanical designation: *Dianthus* L.
Cultivar denomination: 'HILBEAOLWILD'.

BACKGROUND OF THE INVENTION

The present invention relates to a new and distinct cultivar of Carnation plant, botanically known as *Dianthus* L., grown commercially as a container plant and hereinafter referred to by the name 'Hilbeaolwild'.

The new Carnation plant is a product of a planned breeding program conducted by the Inventor in Miniami-Alps City, Yamanashi, Japan. The objective of the breeding program is to create new container Carnation plants with numerous attractive single-type flowers.

The new Carnation plant originated from a cross-pollination made by the Inventor in Miniami-Alps City, Yamanashi, Japan in June, 2010 of a proprietary selection of *Dianthus* L. identified as code number JP 16, not patented, as the female, or seed, parent with a proprietary selection of *Dianthus* L. identified as code number JP 18, not patented, as the male, or pollen, parent. The new Carnation plant was discovered and selected by the Inventor as a single flowering plant from within the progeny of the stated cross-pollination in a controlled greenhouse environment in Miniami-Alps City, Yamanashi, Japan in September, 2011.

Asexual reproduction of the new Carnation plant by terminal cuttings propagated in a controlled greenhouse environment in Miniami-Alps City, Yamanashi, Japan since October, 2011 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbeaolwild'. These characteristics in combination distinguish 'Hilbeaolwild' as a new and distinct Carnation plant:

1. Compact, uniformly mounding and upright to broadly spreading plant habit.
2. Relatively small leaves.
3. Freely flowering habit.
4. Bright pink-colored single flowers with light pink-colored margins.
5. Good container and garden performance.

Plants of the new Carnation differ primarily from plants of the female parent selection in the following characteristics:

1. Plants of the new Carnation are more freely branching than plants of the female parent selection.
2. Plants of the new Carnation have smaller leaves than plants of the female parent selection.
3. Plants of the new Carnation have larger flowers than plants of the female parent selection.
4. Plants of the new Carnation and the female parent selection differ in flower color as plants of the female parent selection have very light pink-colored flowers.

Plants of the new Carnation differ primarily from plants of the male parent selection in the following characteristics:

1. Flowers of plants of the new Carnation have fewer petals than flowers of plants of the male parent selection.
2. Plants of the new Carnation and the male parent selection differ in flower color as plants of the male parent selection have solid pink-colored flowers.

Plants of the new Carnation also can be compared to plants of *Dianthus* L. 'Sunflor Olivia', not patented. In side-by-side comparisons, plants of the new Carnation differ primarily from plants of 'Sunflor Olivia' in flower color as plants of 'Sunflor Olivia' have white-colored flowers with a narrow red-colored ring.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilbeaolwild' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 16° C., night temperatures averaged 12° C. and light levels averaged 7,000 lux. Plants used for the photograph and description were three months old. In the following description, color references are made to The Royal Horticultural Society Colour Chart, 2015 Edition, except where general terms of ordinary dictionary significance are used.

Botanical classification: *Dianthus* L. 'Hilbeaolwild'.

Parentage:

*Female, or seed, parent*.—Proprietary selection of *Dianthus* L. identified as code number JP 16, not patented.

*Male, or pollen, parent*.—Proprietary selection of *Dianthus* L. identified as code number JP 18, not patented.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; growth habit, moderate to low vigor.

*Plant height, soil level to top of foliar plane*.—About 12.8 cm.

*Plant height, soil level to top of floral plane*.—About 13.2 cm.

*Plant diameter or spread*.—About 21.1 cm.

*Lateral branches*.—Branching habit: Freely branching habit with about eight main (basal) stems; each main stem with about three lateral branches; pinching is not required. Length: About 9.3 cm. Diameter: About 2 mm. Internode length: About 3.6 cm. Strength: Strong. Aspect: Upright to outwardly spreading. Texture and luster: Sparsely pubescent; slightly glossy. Color, developing: Close to 142C; at the internodes, close to 145B to 145C. Color, developed: Close to 137A to 137B.

Leaf description:

*Arrangement*.—Opposite, simple; sessile.

*Length*.—About 6.3 cm.

*Width*.—About 1.2 cm.

*Shape*.—Narrowly oblanceolate; slightly curved.

*Apex*.—Acute.

*Base*.—Attenuate; decurrent.

*Margin*.—Finely dentate.

*Texture and luster, upper and lower surfaces*.—Smooth, glabrous; matte.

*Venation pattern*.—Anastomosing.

*Color*.—Developing leaves, upper surface: Close to 143A. Developing leaves, lower surface: Close to 143A to 143B. Fully expanded leaves, upper surface: Close to NN137A; venation, close to NN137A. Fully expanded leaves, lower surface: Close to between 143A and 146B; venation, close to 143A.

Flower description:

*Flower form and flowering habit*.—Single flowers arranged singly or in pairs; freely flowering habit numerous flowers developing during the flowering season; flowers face mostly upright to outwardly.

*Natural flowering season*.—Flowering is continuous from the spring to late summer in The Netherlands; plants begin flowering about eleven weeks after planting.

*Postproduction longevity*.—Flowers last about ten days on the plant; flowers not persistent.

*Fragrance*.—Moderately fragrant; sweet and pleasant.

*Flower buds*.—Length: About 1.8 cm. Diameter: About 5.5 mm. Shape: Elliptic to oblong. Texture and luster: Smooth, glabrous; matte. Color: Close to between N200A and N200B; towards the base, close to 145A; petal apices, close to 61B.

*Flower diameter*.—About 3.3 cm.

*Flower depth*.—About 2.5 cm.

*Petals*.—Quantity and arrangement: Five petals arranged in a single whorl. Length: About 3 cm. Width: About 2 cm. Shape: Spatulate. Apex: Praemorse. Base: Narrowly cuneate. Margin: Irregularly dentate. Texture and luster, upper surface: Mostly smooth and glabrous, proximally, sparsely pubescent; slightly velvety; matte. Texture and luster, lower surface: Smooth, glabrous; slightly velvety; matte. Color: When opening, upper surface: Close to N74A with fine dots, close to 75B; towards the base, radial band of dots, close to 187A, and at the base, close to 145A. When opening, lower surface: Close to 195C, towards the margins and apex, close to NN74C and at the base, close to 145A. Fully opened, upper surface: Close to N74A to N74B; towards the margins and apex, close to 75B; towards the base, close to 187A, and at the base, close to 145A; venation, similar to lamina. With development, color becoming closer to N74B to N74C; towards the margins and apex, close to 75C; towards the base, close to 187A, and at the base, close to 145B. Fully opened, lower surface: Close to 195C, towards the margins and apex, close to 77C to 77D and at the base, close to 145A; venation, similar to lamina.

With development, color becoming closer to 195C, towards the margins and apex, close to 77D and at the base, close to 145B.

*Sepals*.—Quantity and arrangement: Five sepals arranged in a single whorl; proximal 28.5% portion of the sepals are fused into a campanulate-shaped calyx. Calyx length: About 1.4 cm. Calyx diameter: About 6 mm. Sepal length: About 1.4 cm. Sepal width, at base of "free" portion: About 3 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to N200A to N200B; towards the base, close to 145A. When opening, lower surface: Close to 147B; towards the base, close to 145A to 145B. Fully opened, upper surface: Close to 144A; distally, tinged with close to N200A. Fully opened, lower surface: Close to 147B; towards the base, close to 145A.

*Peduncles*.—Length: About 1.1 cm. Diameter: About 1.75 mm. Strength: Moderately strong. Aspect: About 20° from the stem axis. Texture and luster: Smooth, glabrous; slightly glossy. Color: Close to between 137C and 143A.

*Reproductive organs*.—Stamens: Quantity: About ten stamens per flower. Filament length: About 7 mm. Filament color: Close to NN155A; proximally, close to 145D. Anther size: About 1 mm by 0.5 mm. Anther shape: Oblong. Anther color: Close to 161D. Pollen: None observed. Pistils: Quantity: About two per flower. Pistil length: About 1.3 cm. Stigma diameter: About 3 mm. Stigma shape: Pointed, spirally curved. Stigma color: Close to 77D. Style length: About 1 cm. Style color: Close to NN155A. Ovary color: Close to 144A. Fruits and seeds: Fruit and seed development have not been observed on plants of the new Carnation.

Disease & pest resistance: Plants of the new Carnation have not been observed to be resistant to pathogens and pests common to Carnation plants.

Garden performance: Plants of the new Carnation have been observed to have good garden performance and to tolerate high temperatures about 35° C. and to be suitable for USDA Hardiness Zones 5 to 9.

It is claimed:

1. A new and distinct Carnation plant named 'Hilbeaolwild' as illustrated and described.

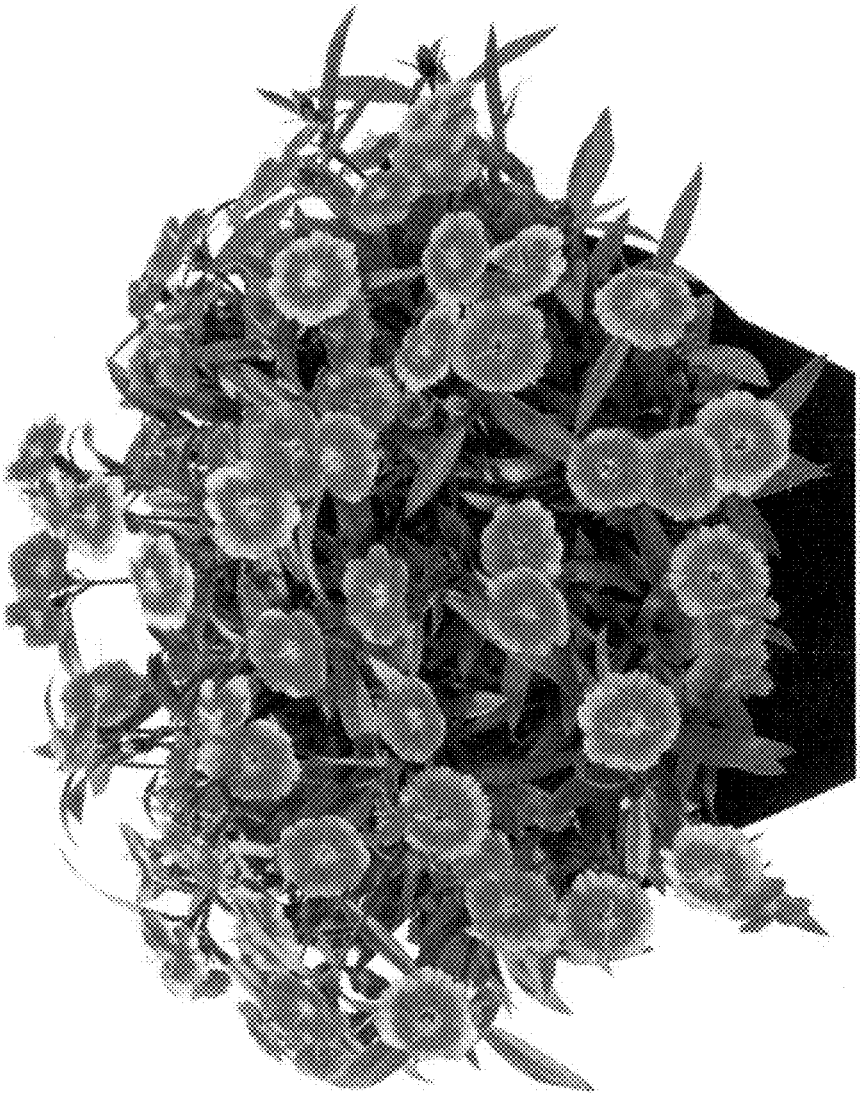

* * * * *